United States Patent [19]
Oelschlager et al.

[11] 3,981,997
[45] Sept. 21, 1976

[54] ANALGESIC COMPOSITIONS COMPRISING 1H- OR RESPECTIVELY 2H-INDAZOLONE-3 (β-MORPHOLINO-ALKOXY) COMPOUNDS

[75] Inventors: Herbert Oelschlager; Uwe Matthiesen, both of Frankfurt am Main; Wilhelm A. Behrendt, Niederweimar, Kr Marburg, Germany

[73] Assignee: Temmler Werke-Vereinigte Chemische Fabriken, Marburg, Lahn, Germany

[22] Filed: May 16, 1975

[21] Appl. No.: 578,270

Related U.S. Application Data

[63] Continuation of Ser. No. 485,633, July 3, 1974, abandoned, which is a continuation of Ser. No. 163,508, July 16, 1971, abandoned.

[30] Foreign Application Priority Data

July 17, 1970   Germany............................ 2035494
July 10, 1971   Germany............................ 2134592

[52] U.S. Cl......................... 424/248; 260/247.5 EP
[51] Int. Cl.²....................................... A61K 31/535

[58] Field of Search .................. 260/247.5 B, 310 C; 424/248

[56]   References Cited
   UNITED STATES PATENTS

| | | |
|---|---|---|
| 3,318,905 | 5/1967 | Palazzo ............................... 260/310 |
| 3,428,634 | 2/1969 | Palazzo ............................ 260/247.5 |
| 3,470,194 | 9/1969 | Palazzo ............................... 260/299 |

*Primary Examiner*—Donald B. Moyer
*Attorney, Agent, or Firm*—Toren, McGeady and Stanger

[57]   ABSTRACT

A process of producing 1H- or respectively 2H-indazolone-3, particularly 3-(β-morpholino-ethoxy)-1H-indazole, 3-(γ-morpholino-propoxy)-1H-indazole and the novel chemical compound 3-(β-morpholino-ethoxy)-4,5,6,7-tetrahydro-2H-indazole by reacting the enolate of 1H-indazolone-3 with morpholino-ethyl-chloride or respectively with γ-morpholino-propyl-chloride, or by reacting the enolate of 4,5,6,7-tetrahydro-2H-indazolone-3 with β-morpholino-ethyl-chloride, under well-defined conditions, resulting in higher yields and optimum purity.

3 Claims, No Drawings

ANALGESIC COMPOSITIONS COMPRISING 1H- OR RESPECTIVELY 2H-INDAZOLONE-3 (β-MORPHOLINO-ALKOXY) COMPOUNDS

This is a Continuation of application Ser. No. 485,633 filed July 3, 1974, which, in turn, was a continuation of Ser. No. 163,508 filed July 16, 1971 both now abandoned.

SUMMARY OF THE INVENTION

This invention relates to a process of producing 1H-indazolone-3 or 2H-indazolone-3 and particularly the compounds 3-(β-morpholino-ethoxy)-1H-indazole according to the following formula

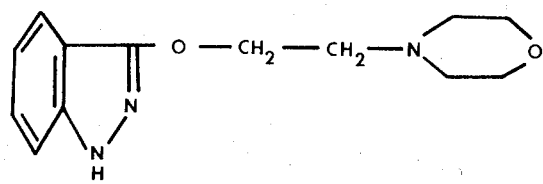

3-(γ-morpholino-propoxy)-1H-indazole according to the followiing formula

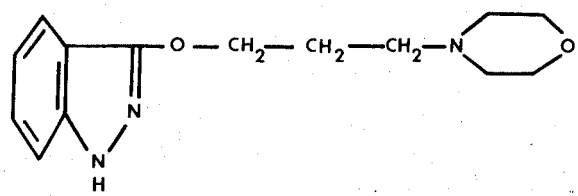

and 3-(β-morpholino-ethoxy)-4,5,6,7-tetrahydro-2H-indazole according to the following formula

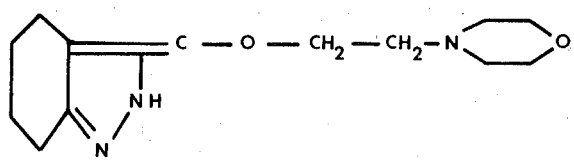

Processes of producing 3-(β-morpholino-ethoxy)-1H-indazole and 3-(γ-morpholino-propoxy)-1H-indazole are known. According to a paper from G. PALAZZO et al. in the *Journal of Medicinal Chemistry*, 9, 38, (1966) on synthesis and pharmacological properties of 1-substituted-3-dimethylalkoxy-1H-indazoles the procedure in the amino alkylation was to firstly form the potassium salt of the 3-hydroxy-1H-indazole which salt reacted, in inert solvents, with the dialkyl-amino-alkyl-chlorides. In this prior art process there were produced, apart from the desired products, also undesired byproducts such as lactames identified in the IR spectrum by a C=O band at 1700 cm$^{-1}$ and the missing C=N oscillation at 1525 cm$^{-1}$. These by-products made it necessary to perform time consuming reprocessing steps by distillation and column chromatography with aluminium oxide, to obtain a pure main product. These purification and treating procedures resulted in low yields.

Surprisingly it has now been discovered that when using aprotic solvents such as "absolute" dioxane, the alkylation reaction may be directed largely towards the formation of the desired enol ethers so that a distillation and likewise a cumbersome column chromatography purification of the obtained final product are are no longer required. Analyses of the non-recrystallized final products obtained according to the process of the present invention showed a good degree of purity in thin layer chromatography and infrared spectroscopy (C=O frequency) investigations.

In another prior art process the above two compounds are produced from the sodium salt of the indazole, and the sodium salt of the indazole and the corresponding ω-morpholino-alkyl-halide in the presence of aprotic solvents such as toluene or dioxane. When testing and redoing the procedure described in the above cited paper for 3-(β-morpholino-ethoxy)-1H-indazole, the yields obtained were below the lower limits of an economical process, quite in contrast to the statements made in this paper. Instead of high yields of 3-dialkyl-amino-alkoxy-1H-indazole the yields obtained in four tests were below 25 % of the theoretical value, subsequent to distillation. Additionally, the compounds produced according to the prior art process are not pure as may be seen by thin layer chromatography, and apart of the desired product (hRF 50) there could be observed two further patches with the hRF values of 20 and 57 respectively. In the IR spectrum appears an additional frequency at 1720 cm$^{-1}$ — obviously C=O — which is absent in the IR spectrum of the compond produced according to the process of the present invention. Further variations likewise appear in the fingerprint field, that is the compounds produced according to the prior art process exhibit a melting range from 102 °C to 111 °C which is increased to 111 °C to 114 °C by dissipative recrystallizations. The final yields amount to approximately 15 % of the theoretical value. Summarizing, the yields obtained in the prior art processes are very low. Additionally, the known processes are rather cumbersome, laborious and uneconomical due to the required processing steps, and particularly the distillation heavily reduces the yield since in this distillation always occur polymerizations notwithstanding the usage of nitrogene and a good vacuum.

It is therefore the object of the present invention to provide a process of producing 1H- or respectively 2H-indazolone-3 which process is economical, may be carried out readily and results in a significantly increased yield while obtaining products having a maximum purity. For achieving this object there is proposed a process of producing such compounds which process is characterized, according to the present invention, by suspending in absolute dioxane the potassium enolate of the 1H-indazolone-3 obtained in vacuum from 1H-indazolone-3 and an equimolar amount of KOH in methanol, after evaporation of the solvent, then adding freshly prepared morpholino-ethyl-chloride obtained by alkylation from the hydrochloride, stirring the mixture in a nitrogene atmosphere at a temperature of about 100 °C, removing the solvent, mixing the residue with water, extracting the residue by means of ether, evaporating the ether extract to dryness and dissolving the thus obtained colorless oil in acetone and adding petroleum ether until the solution becomes cloudy.

According to the present invention there has been discovered furthermore as a novel chemical compound the 3-(β-morpholino-ethoxy)-4,5,6,7-tetrahydro-2H-indazole having the following formula

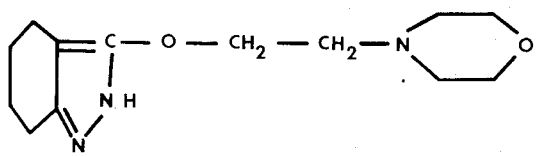

Surprisingly, it has also been found that the compounds indicated in the following are analgetically highly effective, i.e. the 3-(β-morpholino-ethoxy)-1H-indazole having the formula:

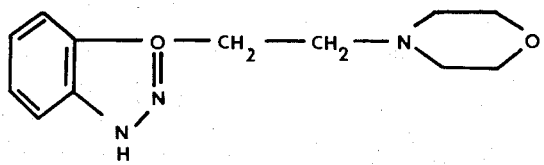

or respectively the hydrobromide thereof, as well as the 3-(γ-morpholino-propoxy)-1H-indazole having the formula:

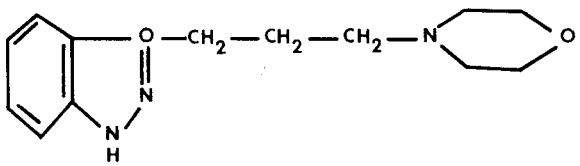

or respectively the hydrochloride thereof, as well as the 3-(β-morpholino-ethoxy)-4,5,6,7-tetrahydro-2H-indazole having the formula:

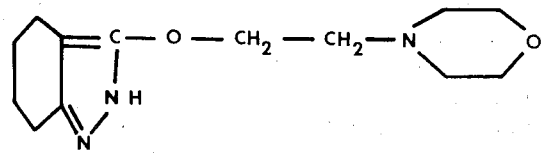

There exists, inter alia, a definite need for so-called "light" analgetica having a better compatability than the mainly used preparations of the analgetica antipyretica series such as acetylsalicylate, phenacetine, pyrazolone derivatives and which surpass these preparations in their effectivity.

Analgetically particularly active are the surprisingly discovered 3-(β-morpholinoethoxy)-1H-indazole or respectively the hydrobromide thereof and the 3-(γ-morpholino-propoxy)-1H-indazole or respectively the hydrochloride thereof as well as the 3-(β-morpholino-ethoxy)-4,5,6,7-tetrahydro-2H-indazole-hydrobromide.

As may be seen from the test results shown in the following Tables I, II, III and IV the compounds of the present invention meet the above stated demands since these compounds while having a better compatability are more effective than the comparative substances.

TABLE I

Toxicity and analgetic effect in the mouse (oral application, dosage specifications in mg/kg body weight, relative to effective substance)

| Substance | Mean lethal dosage ($LD_{50}$) | Mean effective dosage ($ED_{50}$) and relative therapeutic index in the experimental arrangements | | | |
|---|---|---|---|---|---|
| | | Hot plate | | Writhing Test | |
| | | $ED_{50}$ | Th.I. | $ED_{50}$ | Th.I. |
| 3-(β-morpholino-ethoxy)-1H-indazole-hydrobromide | 615 | 142 | 3,53 | 46 | 1,30 |
| codeine phosphate | 265 | 115 | 1,49 | 14 | 1,92 |
| acetylsalicylate | 835 | 500 | 1,67 | 107 | 0,80 |
| aminophenazone | 550 | 283 | 1,00 | 50 | 1,00 |
| phenacetine | 1250 | 530 | 1,71 | 107 | 0,66 |

Th.I. = Therapeutic index ($LD_{10}/ED_{90}$), relative to aminophenazone = 1,00

According to the values shown in Table I and in the following Table III the toxicity and the analgetic effect were determined on male NMRI mice having a body weight from 18 to 20 grams. The mice were kept without food during a period of 18 hours prior to the commencement of the tests. The test substances were administered orally in a methyl-cellulose-mucic (slime) by means of a probe. The observation period for the toxicity tests was 7 days. The determination of the analgetic effect was performed by the hot plate test (modified according to G. WOOLFE and A. D. McDONALD: J. Pharmacol. exp. Ther., 80, 300, 1944) as well as by means of the so-called "writhing tests" in which lactic acid (0.2 ml, 2 %, i.p.) was used as noxe (G. WILHELMI and R. GDYNIA: Arzneimittelforschung, 18, 1525, 1968). The pre-medication periods were 60 minutes in the first test arrangements. In the writhing test the test substances were administered 20 minutes prior to the i.p. injection of lactic acid, and 10 minutes later, i.e. 30 minutes after the administration of the substance, the number of those animals was determined with which the so-called writhing syndrom did not show up. The percentage of the non-reacting animals was used to compute the $ED_{50}$. In the hot plate tests in which the hot plate had a temperature of 56 °C the reaction time of the treated mice was compared once with the values of control group animals whereby licking of the hind paws was regarded as the assessment criterion for the effect of the thermal stimulation. Since the reaction times of the control group animals were log-normally distributed an analgetic effect was assumed in the treated animals if the logarithm of the reaction time of an animal was above the mean value range plus twice the standard deviation of the control group animals. The percentage of animals per dosage for which an analgetoc effect was determined in this manner served to determine the $ED_{50}$, according to the method by J. T. LITCHFIELD and F. WILCOXON (J. Pharmacol, exp. Ther., 96, 99, 1949).

To determine the mean effective dosage $ED_{50}$) determinations of the threshold of pain were made in 30 minute intervals with groups of 12 female rats each, each rat having a body weight from 160 to 360 grams, and these determinations were made prior to and after the treatment with at least 3 doses of the test substances which were administered orally in a 2 % meth-

TABLE II

Analgetic effect on rats (p.o. application, dosage specifications in mg/kg body weight, relative to effective substance)

| Substance | Mean effective dosage ($ED_{50}$) | Relative effectivity, relative to aminophenazone = 1.00 |
|---|---|---|
| 3-($\beta$-morpholino-ethoxy)-1H-indazole-hydrobromide | 34 | 6.84 |
| codeine phosphate | 22 | 10.50 |
| acetylsalicylate | 340 | 0.67 |
| aminophenazone | 229 | 1.00 |
| phenacetine | 123 | 1.86 |

According to Table II and with reference to the method described by A. HERZ (Naunyn-Schmiedeberg's Arch. Pharmakol., 242, 414, 1962) with rats by electrical stimulation of the root of the tail by means of continuously increasing the current a threshold of pain was determined which threshold was characterized in that the animals commenced to squeak in synchronism with the stimulation. When maintaining the selected test conditions these threshold values indicated as percent variations against the initial values prior to the treatment remained practically constant over a period of several hours in a test with control animals. Since these values are furthermore also normally distributed it is possible to quantitatively determine analgetic effects by determining the number of animals whose threshold values exceed during a test run the range defined by the mean value plus twice the standard deviation.

yl-cellulose-mucic by means of a probe. Thereby the number of animals per dosage was determined which exhibited with at least three successive readings an increase of the threshold pain of 14 % or more (analgetic effect). In this manner, not only the intensity but also the duration of the effect were taken into consideration when determining the $ED_{50}$ since the analgesia must be sustained for at least 90 minutes. Apart from the $ED_{50}$ values and the means lethal dosages the table III also shows, for better clarity, the relative therapeutic indices of the various substances, relative to aminophenazone.

The Tables III and IV indicate the test results for the 3-($\beta$-morpholino-ethoxy)-4,5,6,7-tetrahydro-2H-indazole. These results are based upon tests which are different from the above described tests.

TABLE III

Toxicity and analgetic effect on the mouse (oral application, dosage specifications in mg/kg body weight)

| Substance | Mean lethal dosage ($LD_{50}$) | Mean effective dosage ($ED_{50}$) and relative therapeutic index[1] in the experimental arrangements | | | |
|---|---|---|---|---|---|
| | | Hot plate | | Writhing Test | |
| | | $ED_{50}$ | Th.I.[1] | $ED_{50}$ | Th.I.[1] |
| 3-($\beta$-morpholino-ethoxy)-4,5,6,7-tetrahydro-2H-indazole | 1720 | 540 | 2.67 | 94 | 2.07 |
| acetylsalicylate | 835 | 500 | 1.88 | 107 | 0.91 |
| aminophenazone | 550 | 283 | 1.00 | 50 | 1.00 |
| phenacetine | 1250 | 530 | 1.93 | 107 | 0.74 |

[1]relative therapeutic index = $LD_{10}/ED_{50}$, relative to aminophenazone = 1.00

TABLE IV

Toxicity and analgetic effect on the rat (oral application, dosage specifications in mg/kg body weight)

| Substance | Mean lethal dosage ($LD_{50}$) | Mean effective dosage ($ED_{50}$) in the experimental arrangement of HERZ (electrical stimulation of root of the tail) | |
|---|---|---|---|
| | | $ED_{50}$ | relative therapeutic index[1] |
| 3-($\beta$-morpholino-ethoxy)-4,5,6,7-tetrahydro-2H-indazole | 1600 | 143 | 1.62 |
| acetylsalicylate | 1400 | 340 | 0.28 |
| aminophenazone | 1350 | 229 | 1.00 |

[1]relative therapeutic index = $LD_{10}/ED_{90}$, relative to aminophenazone = 1.00

The Examples described in the following serve to illustrate the process of the present invention.

EXAMPLE I 50 millimole of potassium enolate of the 1H-indazolone-3 obtained from 1-H-indazolone-3 and an equimolar amount of KOH in methanol, after evaporation of the solvent in vacuum, are suspended in 100 ml of absolute dioxane. 55 millimole of morpholino-ethyl-chloride freshly prepared by alkylation from the hydrochloride are then added and the mixture is stirred in a nitrogene atmosphere during 6 hours at 100 °C. After cooling and removing the solvent in vacuum the residue is mixed with water and extracted by means of ether. The ether extract is then vibrated with silica gel (0.2–0.5 mms, Merck) and then filtered and concentrated to dryness. The almost colorless oil is then dissolved in a small quantity of acetone and mixed with petroleum ether until cloudiness is obtained. Then the crystallization commences. In this manner there is obtained 3-($\beta$-morpholino-ethoxy)-1H-indazole in the form of colorless crystals.

FP 113 °C to 115 °C. Yield 60 % of the theoretical value.

The product is homogeneous as may be shown by thin layer chromatography analysis (DC) and the IR spectrum. The hydrobromide of the product melts between 186 °C and 190 °C (from isopropanol/ether).

EXAMPLE II 3-($\gamma$-morpholino-propoxy)-1H-indazole is prepared analogously to Example I by reacting the potassium enolate with $\gamma$-morpholino-propyl-chloride. 3-($\gamma$-morpholino-propoxy)-1H-indazole. A viscous oil was obtained and crystallized as monohydrate.

FP. 93 °C to 95 °C. Yield 59 % of the theoretical value. Hydrochloride: FP. 195 °C to 200 °C from isopropanol/ether.

EXAMPLE III

For producing 3-($\beta$-morpholino-ethoxy)-4,5,6,7-tetrahydro-2H-indazole there is formed as in Example I the enolate of the 4,5,6,7-tetrahydror-2H-indazolone-3 and reacted in absolute dioxane with $\beta$-morpholino-ethyl-chloride. The thus obtained pale oil is dissolved in a small amount of benzene and mixed with a large quantity of petroleum ether, and then crystallization initiates.

3-($\beta$-morpholino-ethoxy)-4,5,6,7-tetrahydro-2H-indazole colorless crystals.

FP. 65 °C. Yield 68 % of the theoretical value. Hydrobromide: 149 °C tp 153 °C from ispropanol/ether.

By means of the process of the present invention high yields of the end products are obtained, in a maximum purity. Yield reducing distillations are eliminated. No purification via a salt is required.

What is claimed is:

1. A pharmaceutical composition consisting essentially of an analgesically effective amount of 3-($\beta$-morpholino-ethoxy)-4,5,6,7-tetrahydro-2H-indazole-hydrobromide and an inert carrier.

2. A pharmaceutical composition consisting essentially of an analgesically effective amount of 3-($\beta$-morpholino-ethoxy-)iH-indazole or the hydrobromide thereof and an inert carrier.

3. A pharmaceutical composition consisting essentially of an analgesically effective amount of 3-($\gamma$-morpholino-propoxy)-iH-indazole or the hydrochloride thereof and an inert carrier.

* * * * *

UNITED STATES PATENT OFFICE
CERTIFICATE OF CORRECTION

Patent No. 3,981,997        Dated September 21, 1976

Inventor(s) Herbert Oelschläger et al

It is certified that error appears in the above-identified patent and that said Letters Patent are hereby corrected as shown below:

In the heading of the Patent [30] should read as follows:

--[30] Foreign Application Priority Data

July 17, 1970    Germany........2035494
    July 12, 1971    Germany........2134592--.

Signed and Sealed this

Ninth Day of November 1976

[SEAL]

Attest:

RUTH C. MASON
*Attesting Officer*

C. MARSHALL DANN
*Commissioner of Patents and Trademarks*